United States Patent [19]
Hall et al.

[11] 4,186,739
[45] Feb. 5, 1980

[54] ATHLETIC GARMENT

[76] Inventors: Gwendolyn L. Hall; Bradley G. Hall, both of 60 Redcar Ave., Islington, Toronto, Canada, M9B 1K1

[21] Appl. No.: 826,149
[22] Filed: Aug. 19, 1977
[51] Int. Cl.² .................................................. A61F 5/40
[52] U.S. Cl. .................................................. 128/158
[58] Field of Search .............................. 128/158–160; 24/245 A, 245 R, 247; 2/240, 409, 22, 24

[56] References Cited

U.S. PATENT DOCUMENTS

| | | | |
|---|---|---|---|
| 452,529 | 5/1891 | Pfister | 128/160 |
| 808,495 | 12/1905 | Ware | 128/160 |
| 1,421,077 | 6/1922 | Goldsmith | 128/160 |
| 2,553,353 | 5/1951 | Binder et al. | 128/159 |
| 2,627,639 | 2/1953 | Eilersten | 24/245 A |
| 3,422,504 | 1/1969 | Brown | 24/245 A |
| 3,788,314 | 1/1974 | Noreen | 128/159 |
| 3,880,160 | 4/1975 | Hall | 128/158 |

FOREIGN PATENT DOCUMENTS

| | | | |
|---|---|---|---|
| 129533 | 10/1948 | Australia | 128/159 |
| 462426 | 5/1937 | United Kingdom | 128/159 |
| 494393 | 10/1938 | United Kingdom | 128/158 |

*Primary Examiner*—Lawrence W. Trapp

[57] ABSTRACT

An athletic supporter has a waist band of a wide elastic portion with a narrower upper border strip. Preferably the ends meet at the front in a wide downwardly directed V.

10 Claims, 9 Drawing Figures

ATHLETIC GARMENT

This invention relates to improvements in athletic supporters for ladies, for men and for children.

In a preferred aspect of the invention, the invention comprises an athletic supporter for a male or female, including a waist-band portion and a pouch attached to the centre of the front of the band and attached by conventional straps to the rear thereof, where the waist band portion comprises a wide relatively light portion of elastic material extending about the body. This material, is preferably of the type stretchable in all directions often known as two-way stretch material. There is attached to the wide portion adjacent the upper edge, a narrower band of elastic material attached in overlapping relationship to extend as high as or higher than the upper edge of the wide waist band. Such band material preferably stretches only in the direction about the waist of the wearer. The effect of the attached band of elastic material is to prevent "rolling" of the upper edge, and of the band itself under the flexure and stresses of use, and thus to increase the functionality and comfort of the garment. A second such narrower elastic band is, preferably also attached to the wide waist band adjacent the lower edge thereof.

In another aspect of the invention, the invention comprises an athletic supporter for a male or female; including a waist-band portion of elastic material and a pouch attached to the centre of the front of the waist band and attached by conventional straps to the rear thereof, where the waist-band portion, with attached elastic band or bands as described in the previous paragraph, has its ends overlapping at the front of the band. The ends overlapping at the front of the band overlap in non-parallel relation and are sewn to form an upwardly directed shallow V. The result is an overlapping connected (by sewing) area, at the ends, which approximates an upwardly diverging triangle from a point adjacent the attachment to the waist band forward end of the pouch. This double thickness triangle acts to effectively transfer the downward stresses from the pouch connection to the upper band of the supporter. In addition, the non-parallel connection of the waist band ends, results in the band, instead of resting horizontally on the waist of the wearer, in having an upward component from the front to the back, about both sides. The transfer of stress along this upward component tends to cause the upper edge of the band to remain straight rather than wrinkled, and the band is extremely comfortable in use, in contrast to the supporters of the prior art and provides a balanced support for the pouch and cup which maintains them in position in the wide variety of body attitudes normally encountered in hockey.

In another aspect of the invention, the invention comprises an athletic supporter for a male or female, including a waist band portion and a pouch connection and including depending connections, with fasteners on the end, for attachment to the athletic socks or stockings of the wearer. The provision of a supporter with such depending connections is known from U.S. Pat. No. 3,880,160 issued Apr. 29, 1975, to Gwendolyn L. Hall. However, there is herein described with a novel fastener for use with such supporter and for use with supporters of other types. The novel fastener includes a body designed to receive a connecting strap to the supporter for attachment of said body to said supporter. The fastener is designed to provide secure support for hockey or other stockings under collision or falling and is designed to be easily operated with one hand by the young and handicapped. The body defines a T-shaped slot with the cross bar of the T perpendicular to the line from the T-shaped slot to the location of the strap attachment. The upright of the T of the T slot extends toward the strap slot. A relatively flat button is attached to the body by a relatively thin flexible member extending from the top of the body opposite the T shaped slot. The button is dimensioned, with a thickness of sock thereover, to pass edgewise through the cross-bar of the T-shaped slot and thereafter to be flattened relative to the body, to be retained thereafter from retraction through the slot when under the normal pulling action of the sock. As the button is passed edgewise through the slot, the thin strap, which will also have sock material thereover will be moved into the slot forming the upright of the T thus further increasing the strength of the coupling between the sock and the body.

In another aspect of the invention, the invention comprises an athletic supporter particularly adapted for females, and includes a special protective cup, and means for housing it. The special cup includes a flexible (preferably of the constitution of sponge rubber) extension attached to the cup and extending rearwardly thereof to protect the female wearer in the areas rearwardly of the cup. The female supporter is provided with a pocket defining an area to receive the normal cup and defining an elongated area to receive the extension.

In drawings which illustrate a preferred embodiment of the invention:

The sewing for attachment of the connected members is not shown herein as the methods and techniques of sewing are well known to those skilled in the art.

Figure 1:
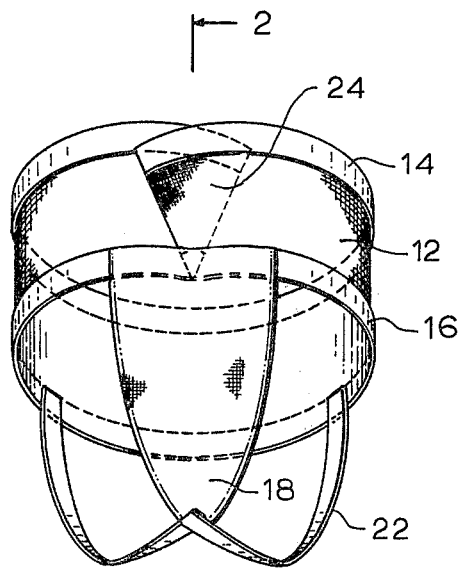
FIG. 1 shows a perspective view of a male supporter in accord with the invention.

In FIG. 1 is shown a male athletic supporter 10 including a portion of elastic wide band material 12 preferably of an open weave or net material. Attached adjacent the upper edge of waist band portion 12 is a strong flat elastic band 14 narrower than the waist band. The upper edge of band 14 is at least as high, and preferably higher, as shown, than the upper edge of the wide portion 12. Preferably attached adjacent the lower edge of the waist band is a second strong flat elastic band 16 also narrower than the wide portion 12 and overlapping it, so that the lower edge of the elastic band 14 is at least as low and preferably lower than the lower edge of the wide portion 12. Waist band material 12 is elastic as well as bands 14 and 16 so that these members may stretch together to comply with the waist of a user. The bands 14 and 16 are attached to waist band material 12 by stitching, not shown, but which will be arranged to allow the expansion and contraction of the joined bands. The term 'waist band' herein refers to the wide elastic portion together with any attached elastic bands.

Best results in avoiding 'rolling' of the combined bands 12, 14 and 16 or 12 and 14 and for general comfort are achieved when the wide portion 12 is of material stretchable in all directions and the bands 14 and 16 are designed to stretch only about the waist. It will be noted that bands 12 and 14 need not be separate from the wide portion 12 but may be extensions of that material, preferably doubled over and sewn to define the band 12 or 14 so as to permit stretching only in the direction about the waist.

The waist band is sewn at the front in the manner hereinafter described and is sewn to a pouch 18 of conventional form at the front. The pouch 18 is provided with an inner layer 20 which is, at its central portion, unattached to the outer layer, to allow insertion of a protective cup in the pouch. A pair of elastic straps 22 join the rear of the pouch to spaced locations at the rear of the supporter.

The waist band, as shown in FIG. 1, is sewn at the front (by sewing not shown) to join the ends of the waist band in overlapping relationship. The overlapping ends are joined to be non-parallel but to form an upwardly directed shallow V. The result is an overlapping sewn area at the ends which approximates a triangle 24 upwardly directed from a point adjacent the attachment thereto of the forward end of the pouch. This double thickness triangle 24 acts to effectively transfer the downward stresses from the pouch connection to the upper band of the supporter. In addition, the non-parallel connection of the waist band ends, results in the band, instead of resting horizontally on the waist of the wearer, having an upward component from the front to the back, about both sides. The transfer of stress rearwardly upwardly about both sides ensures that the upper edges of the band is straight rather than wrinkled, and is comfortable in use, in contrast to the supporters of the prior art.

The elastic band 14 overlapping the wide portion 12 at the top reduces the chance of "rolling" of the upper edge of the band and the consequent discomfort of the wearer.

Figure 3:
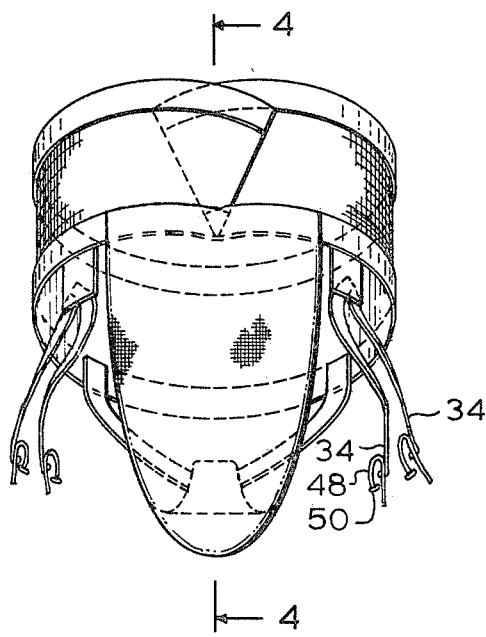
FIG. 3 shows a perspective view of a female supporter in accord with the invention and showing the supports for socks or stockings in accord therewith.
Figure 4:
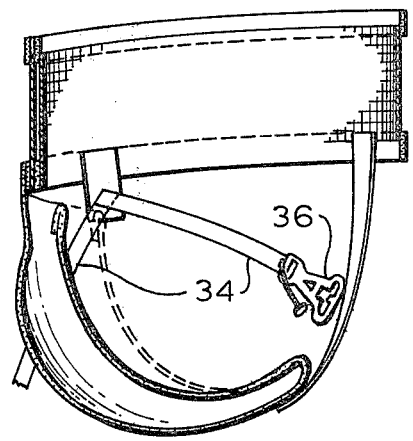
FIG. 4 shows a cross-section along the lines 4—4 of FIG. 3.
Figure 5:
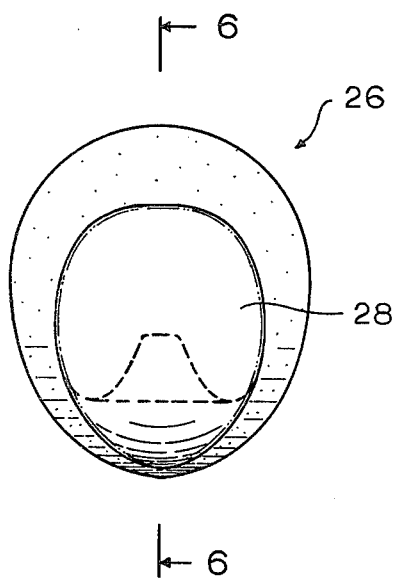
FIG. 5 shows a front view of a female cup.
Figure 6:
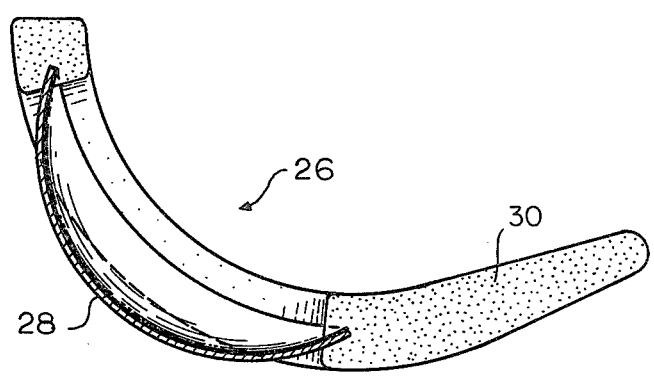
FIG. 6 shows a cross-section along the lines 6—6 of FIG. 5.
Figure 7:
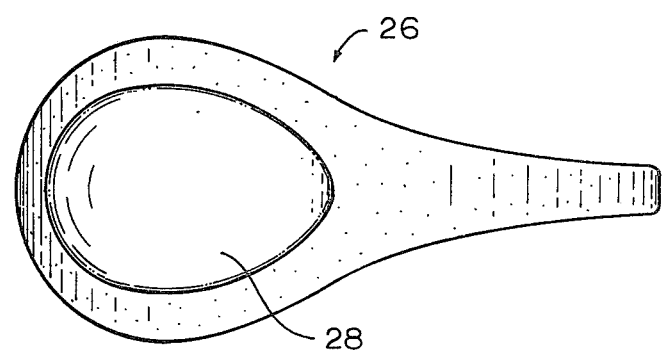
FIG. 7 shows a bottom view of the female cup.

FIGS. 3 and 4 show a supporter having the features described in connection with FIG. 1 but being designed for a female. As shown in FIGS. 3 and 4, there is provided an elongated pouch shaped to receive the protector 26 of FIGS. 5-7. The pouch is preferably made of material which stretches in all directions. The protector 26 comprises a cup shaped as in the conventional male version with foam rubber extending there around and, in addition, a foam rubber extent 30 extending rearwardly thereof and designed to provide protection for the female wearer rearwardly of the cup 28. As stated, the pouch on the supporter of FIGS. 3 and 4 is shaped to receive the protector of FIGS. 5-7.

Figure 2:
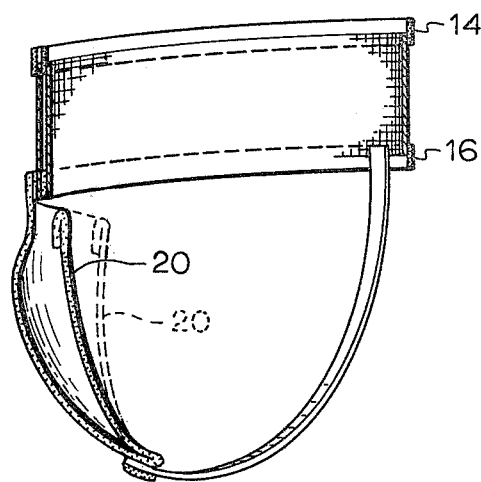
FIG. 2 shows a cross-section along the lines 2—2 of FIG. 1.
Figure 8:
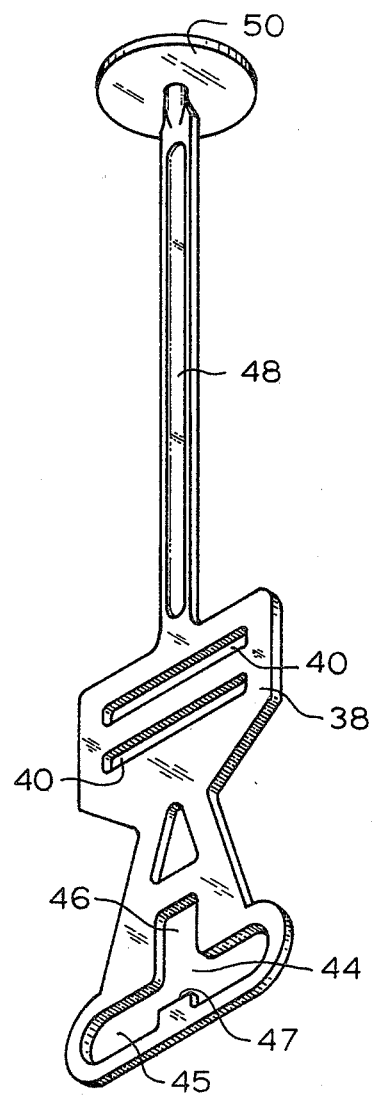
FIG. 8 shows a perspective of a fastener in accord with the invention.
Figure 9:
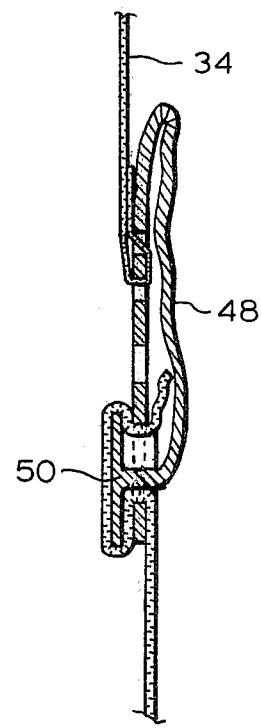
FIG. 9 shows a cross-section of the fastener of FIG. 8 in the action of holding a hockey sock.

FIGS. 3 and 4 also show a pair of straps 34 depending from each side of the socket of the waist-band having fasteners 36 on the end for attachment to hockey socks or other sports stockings. Such straps and fasteners may, of course, be used with the supporter of FIGS. 1 and 2 and on supporters which do not have the other inventive features. The fasteners 36, shown in detail in FIGS. 8 and 9, are of novel design, as far as known to applicant.

The fastener 36 comprises a body 38 provided with attachment means for straps 34. In the preferred embodiment the attachment means comprises a pair of slots 40 through which a strap 34 may be looped and sewn, (by sewing not shown) as best shown in FIG. 9. It will be noted that the end of strap 34 and the portion of the strap to which it attaches to form a loop may be made of "Velcro" and fastened in the matter used with that material rather than by sewing. At one end of the body is provided a T-shaped slot 44 having the cross-bar 45 of the T transverse to the line joining the slot 44 to slots 40 and the upright 46 of the T extending toward slots 40. As small stub 47 is preferably provided projecting into the central portion of the cross-bar of the T toward upright 46. Projecting from the end of body 38, opposite to that containing the T-shaped slots, is a flexible extent 48 dimensioned to be received within the upright 46 of the T (with a thickness of hockey sock on each side thereof). On the end of extent 48 remote from the body is a button 50 designed to be received edgewise through the cross-bar 45 of the T-shaped slot with a thickness of sock wrapped thereon. In the preferred embodiment, this implies that the cross-bar portion 45 of the slot must be wide enough to receive the button with a thickness of sock wrapped thereon at the inward projection of stub 47.

The fastener 36 is attached to the stocking by being inserted in the stocking material and with such material wrapped therearound, is passed edgewise through the cross-bar 45 of the T-shaped slot. The button and material is then flattened to assume the position shown in FIG. 9. In the process of insertion and flattening of the button, the flexible extent 48 is received in upright slot 46 of the T. The stocking is, by the above means, firmly attached to the fastener. The firmness and security of the attachment is found to be increased where the stub 47 is provided projecting into the slot.

The flexible extent 48 is preferably made of slightly stretchable material.

The fastener as shown in FIGS. 8 and 9 is preferably made from a single plastic moulding. However, if desired the fastener of FIGS. 8 and 9 may be made of separate materials attached to each other. For example the fastener may be constructed with body 38 and button 50 of rigid material with a separate flexible member 48 connecting them. The sewing for attachment of the straps and other sewn members is not shown as this is well known to those skilled in the art.

We claim:
1. An athletic supporter including:
a waist band,
a pouch connected to the centre of the front of said waist band and two straps connected to the rear of said waist band,
wherein the waist band comprises a relatively wide elastic portion of a length to extend about the waist of the wearer,
wherein the ends of said waist band are arranged to be connected, at the front of the wearer's body, in overlapping, non-parallel relationship,
wherein the end edges of the waist band diverge in an upward direction and at the lower end connect to each other near the pouch over a circumferential extent, short relative to and approximately centered with respect to the circumferential extent of the top of the pouch.

2. An athletic supporter, as claimed in claim 1, wherein said waist band includes a narrower flat elastic band, of a length to extend about the body of the wearer, attached to said wide portion, so that the upper edge, in use, of said band is located to be at least as high as the upper edge of said wide portion, and wherein the wide portion of said band is stretchable in all directions.

3. An athletic supporter, as claimed in claim 2, wherein said waist band includes a second narrower flat elastic band, of a length to extend about the body of the wearer, attached to said wide portion so that the lower edge, in use, of said second band is located to be at least as low as the lower edge of said wide portion, and wherein the wide portion of said band is stretchable in all directions.

4. A fastener for attachment to hockey socks, comprising:
a body,
defining, towards one end, means for attachment to supporting means,
and defining, towards the other end, a T-shaped slot wherein the upright of the T extends towards the attachment means,
a button having greater transverse dimensions than thickness and defining opposed faces spaced by a thickness dimension less than the small dimension of the cross-bar of the T-shaped slot,
said button having dimensions transverse to the thickness dimension allowing it to pass edgewise through the cross-bar of the T-shaped slot with sock material on both sides thereof and a minimum transverse dimension greater than the small dimension of the said cross-bar,
said button being attached to said body by a flexible strip attached to said button approximately centrally of one of said transverse faces,
said strip being dimensioned with sock material thereover to be received in the upright of said T-shaped slot.

5. A fastener as claimed in claim 4 wherein a projection extends into the cross-bar of the T-shaped slot on the side thereof remote from the upright of the T and projecting theretowards, said projection being dimensioned to allow passage of the button therepast with sock material thereover edgewise therepast.

6. A supporter as claimed in claim 1 having a pair of straps depending from each side thereof, there being attached to each said strip, a fastener comprising:
a body,
defining, towards one end, means for attachment to supporting means,
and defining, towards the other end, a T-shaped slot wherein the upright of the T extends towards the attachment means,
a button having greater transverse dimensions than thickness and defining opposed faces spaced by a thickness dimension less than the small dimension of the cross-bar of the T-shaped slot,
said button having dimensions transverse to the thickness dimension allowing it to pass edgewise through the cross-bar of the T-shaped slot with sock material on both sides thereof and a minimum transverse dimension greater than the small dimension of the said cross-bar,
said button being attached to said body by a flexible strip attached to said button approximately centrally of one of said transverse faces,
said strip being dimensioned with sock material thereover to be received in the upright of said T-shaped slot.

7. A fastener for athletic socks or stocking comprising:
a body,
defining, towards one end, means for attachment to supporting means,
and defining, towards the other end, a T-shaped slot wherein the upright of the T extends towards the attachment means,
a button having greater transverse dimensions than thickness and defining opposed faces spaced by a thickness dimension less than the small dimension of the cross-bar of the T-shaped slot,
said button having dimensions transverse to the thickness dimension allowing it to pass edgewise through the cross-bar of the T-shaped slot with sock material on both sides thereof and a minimum transverse dimension greater than the small dimension of the said cross-bar,
said button being attached to said body by a flexible strip attached to said button approximately centrally of one of said transverse faces,
said strip being dimensioned with sock material thereover to be received in the upright of said T-shaped slot.

8. A fastener as claimed in claim 7 wherein a projection extends into the cross-bar of the T-shaped slot on the side thereof remote from the upright of the T and projecting theretowards, said projection being dimensioned to allow passage of the button therepast with sock material thereover edgewise therepast.

9. An athletic supporter including:
a waist band,
a pouch permanently connected to the centre of the front of said waist band and to two straps connected to the rear of said waist band,
said pouch being designed for receipt of a protective cup,
wherein the waist band comprises a relatively wide elastic portion stretchable in all directions of a length to extend about the waist of the wearer,
and a narrower flat elastic band of a length to extend about the body of the wearer, attached to said wide portion so that the upper edge, in use, of said band is located to be at least as high as the upper edge of said wide portion,
a pair of straps depending from said band, there being attached to the lower end of each said strap, a fastener comprising:
a body,
defining, towards one end, means for attachment to supporting means,
and defining, towards the other end, a T-shaped slot wherein the upright of the T extends towards the attachment means,
a button having greater transverse dimensions than thickness and defining opposed faces spaced by a thickness dimension less than the small dimension of the cross-bar of the T-shaped slot,
said button having dimensions transverse to the thickness dimension allowing it to pass edgewise through the cross-bar of the T-shaped slot with sock material on both sides thereof and a minimum transverse dimension greater than the small dimension of the said cross-bar,
said button being attached to said body by a flexible strip attached to said button approximately centrally of one of said transverse faces,
said strip being dimensioned with sock material thereover to be received in the upright of said T-shaped slot.

10. An athletic supporter including:
a waist band,
a pouch permanently connected to the centre of the front of said waist band and to two straps connected to the rear of said waist band,
said pouch being designed for receipt of a protective cup,
wherein the waist band comprises a relatively wide elastic portion stretchable in all directions of a length to extend about the waist of the wearer,
and a narrower flat elastic band, of a length to extend about the body of the wearer, attached to said wide portion so that the upper edge, in use, of said band is located to be at least as high as the upper edge of said wide portion,
including a second narrower flat elastic band, of a length to extend about the body of the wearer, attached to said wide portion so that the lower edge, in use, of said second band is located to be at least as low as the lower edge of said wide portion,
a pair of straps depending from the front of said supporter, there being attached to the lower end of each said strap, a fastener comprising:

a body,
defining, towards one end, means for attachment to supporting means,
and defining, towards the other end, a T-shaped slot wherein the upright of the T extends towards the attachment means,
a button having greater transverse dimensions than thickness and defining opposed faces spaced by a thickness dimension less than the small dimension of the cross-bar of the T-shaped slot,
said button having dimensions transverse to the thickness dimension allowing it to pass edgewise through the cross-bar of the T-shaped slot with sock material on both sides thereof and a minimum transverse dimension greater than the small dimension of the said cross-bar,
said button being attached to said body by a flexible strip attached to said button approximately centrally of one of said transverse faces,
said strip being dimensioned with sock material thereover to be received in the upright of said T-shaped slot.

* * * * *